(12) United States Patent
Kilian et al.

(10) Patent No.: US 9,029,137 B2
(45) Date of Patent: May 12, 2015

(54) ACP PROMOTER

(71) Applicants: Oliver Kilian, Alameda, CA (US);
Bertrand Vick, Emeryville, CA (US)

(72) Inventors: Oliver Kilian, Alameda, CA (US);
Bertrand Vick, Emeryville, CA (US)

(73) Assignee: Aurora Algae, Inc., Hayward, CA (US)

( * ) Notice: Subject to any disclaimer, the term of this patent is extended or adjusted under 35 U.S.C. 154(b) by 0 days.

(21) Appl. No.: 13/874,366

(22) Filed: Apr. 30, 2013

(65) Prior Publication Data

US 2013/0289262 A1 Oct. 31, 2013

Related U.S. Application Data

(60) Provisional application No. 61/640,084, filed on Apr. 30, 2012.

(51) Int. Cl.
*C12N 15/79* (2006.01)
*C12N 15/113* (2010.01)

(52) U.S. Cl.
CPC .............. *C12N 15/113* (2013.01); *C12N 15/79* (2013.01)

(58) Field of Classification Search
None
See application file for complete search history.

(56) References Cited

U.S. PATENT DOCUMENTS

| | | |
|---|---|---|
| 1,926,780 A | 9/1933 | Lippincott |
| 3,468,057 A | 9/1969 | Buisson et al. |
| 3,962,466 A | 6/1976 | Nakabayashi |
| 4,003,337 A | 1/1977 | Moore |
| 4,267,038 A | 5/1981 | Thompson |
| 4,365,938 A | 12/1982 | Warinner |
| 4,535,060 A | 8/1985 | Comai |
| 4,658,757 A | 4/1987 | Cook |
| 5,105,085 A | 4/1992 | McGuire et al. |
| 5,478,208 A | 12/1995 | Kasai et al. |
| 5,527,456 A | 6/1996 | Jensen |
| 5,661,017 A | 8/1997 | Dunahay et al. |
| 5,668,298 A | 9/1997 | Waldron |
| 5,723,595 A | 3/1998 | Thompson et al. |
| 5,823,781 A | 10/1998 | Hitchcock et al. |
| 6,027,900 A | 2/2000 | Allnutt et al. |
| 6,117,313 A | 9/2000 | Goldman et al. |
| 6,143,562 A | 11/2000 | Trulson et al. |
| 6,166,231 A | 12/2000 | Hoeksema |
| 6,297,054 B1 | 10/2001 | Maliga et al. |
| 6,372,460 B1 | 4/2002 | Gladue et al. |
| 6,448,055 B1 | 9/2002 | Shimizu et al. |
| 6,736,572 B2 | 5/2004 | Geraghty |
| 6,750,048 B2 | 6/2004 | Ruecker et al. |
| 6,831,040 B1 | 12/2004 | Unkefer et al. |
| 6,871,195 B2 | 3/2005 | Ryan et al. |
| 7,244,609 B2 | 7/2007 | Drocourt et al. |
| 7,333,195 B2 | 2/2008 | Kreiss et al. |
| 7,381,326 B2 | 6/2008 | Haddas |
| 7,410,637 B2 | 8/2008 | Sayre et al. |
| 7,449,568 B2 | 11/2008 | Fukuda et al. |
| 7,547,551 B2 | 6/2009 | Schuler et al. |
| 8,039,230 B2 | 10/2011 | Otte et al. |
| 8,119,859 B2 | 2/2012 | Vick et al. |
| 8,314,228 B2 | 11/2012 | Kilian et al. |
| 8,318,482 B2 | 11/2012 | Vick et al. |
| 8,440,805 B2 | 5/2013 | Kilian et al. |
| 8,685,723 B2 | 4/2014 | Vick et al. |
| 8,709,765 B2 | 4/2014 | Bailey et al. |
| 8,722,359 B2 | 5/2014 | Kilian et al. |
| 8,753,879 B2 | 6/2014 | Kilian et al. |
| 8,759,615 B2 | 6/2014 | Vick et al. |
| 8,785,610 B2 | 7/2014 | Kilian et al. |
| 8,809,046 B2 | 8/2014 | Kilian et al. |
| 2003/0049720 A1 | 3/2003 | Hoshino et al. |
| 2003/0140021 A1 | 7/2003 | Ryan et al. |
| 2003/0143743 A1 | 7/2003 | Schuler et al. |
| 2003/0199490 A1 | 10/2003 | Antoni-Zimmermann et al. |
| 2003/0211089 A1 | 11/2003 | Sayre et al. |
| 2004/0161364 A1 | 8/2004 | Carlson |
| 2004/0262219 A1 | 12/2004 | Jensen |
| 2005/0064577 A1 | 3/2005 | Berzin |
| 2005/0095569 A1 | 5/2005 | Franklin |
| 2005/0124010 A1 | 6/2005 | Short et al. |
| 2005/0170479 A1 | 8/2005 | Weaver et al. |
| 2005/0181345 A1 | 8/2005 | Bradbury et al. |
| 2005/0260553 A1 | 11/2005 | Berzin |
| 2006/0031087 A1 | 2/2006 | Fox et al. |
| 2006/0044259 A1 | 3/2006 | Hotelling et al. |
| 2006/0045750 A1 | 3/2006 | Stiles |
| 2006/0101535 A1 | 5/2006 | Forster et al. |
| 2006/0122410 A1 | 6/2006 | Fichtali et al. |
| 2006/0155558 A1 | 7/2006 | Corpening |
| 2006/0166243 A1 | 7/2006 | Su et al. |
| 2006/0166343 A1 | 7/2006 | Hankamer et al. |
| 2006/0192690 A1 | 8/2006 | Philipp |

(Continued)

FOREIGN PATENT DOCUMENTS

| | | |
|---|---|---|
| CN | 1627764 | 6/2005 |
| CN | 1867140 | 11/2006 |
| CN | 1956335 | 5/2007 |
| CN | 101289659 | 10/2008 |
| CN | 102164492 A1 | 8/2011 |
| CN | 102858980 A1 | 1/2013 |
| CN | 103974966 A | 8/2014 |
| EP | 2297326 A1 | 3/2011 |
| EP | 2491124 A1 | 8/2012 |
| HK | 1175201 A1 | 6/2013 |

(Continued)

OTHER PUBLICATIONS

GenBank Accession No. ER498938 GI:133929743 May 22, 2007.*
International Search Report mailed Sep. 16, 2009 for Application No. PCT/US2009/004296, filed Jul. 24, 2009.
Written Opinion of the International Searching Authority mailed Sep. 16, 2009 for Application No. PCT/US2009/004296, filed Jul. 24, 2009.

(Continued)

*Primary Examiner* — Jehanne Sitton
(74) *Attorney, Agent, or Firm* — Carr & Ferrell LLP

(57) ABSTRACT

Isolated nucleotide sequences encoding a promoter of the Acyl Carrier Protein ("ACP").

1 Claim, 15 Drawing Sheets

(56) References Cited

U.S. PATENT DOCUMENTS

| | | | |
|---|---|---|---|
| 2007/0178451 A1 | 8/2007 | Deng et al. |
| 2008/0118964 A1 | 5/2008 | Huntley et al. |
| 2008/0120749 A1 | 5/2008 | Melis et al. |
| 2008/0160488 A1 | 7/2008 | Younkes et al. |
| 2008/0160591 A1 | 7/2008 | Willson et al. |
| 2008/0194029 A1 | 8/2008 | Hegemann et al. |
| 2008/0268539 A1 | 10/2008 | Singh et al. |
| 2008/0293132 A1 | 11/2008 | Goldman et al. |
| 2009/0029445 A1 | 1/2009 | Eckelberry et al. |
| 2009/0061493 A1 | 3/2009 | Trimbur et al. |
| 2009/0061928 A1 | 3/2009 | Lee et al. |
| 2009/0148931 A1 | 6/2009 | Wilkerson et al. |
| 2009/0234146 A1 | 9/2009 | Cooney et al. |
| 2009/0317857 A1 | 12/2009 | Vick et al. |
| 2009/0317878 A1 | 12/2009 | Champagne et al. |
| 2009/0317904 A1 | 12/2009 | Vick et al. |
| 2009/0319338 A1 | 12/2009 | Parks et al. |
| 2009/0325270 A1 | 12/2009 | Vick et al. |
| 2010/0022393 A1 | 1/2010 | Vick |
| 2010/0068772 A1 | 3/2010 | Downey |
| 2010/0100520 A1 | 4/2010 | Dargue et al. |
| 2010/0198659 A1 | 8/2010 | Meltzer et al. |
| 2010/0210003 A1 | 8/2010 | King et al. |
| 2010/0210832 A1 | 8/2010 | Kilian et al. |
| 2010/0314324 A1 | 12/2010 | Rice et al. |
| 2010/0323387 A1 | 12/2010 | Bailey et al. |
| 2010/0330643 A1 | 12/2010 | Kilian et al. |
| 2011/0015415 A1 | 1/2011 | Singh et al. |
| 2011/0059495 A1 | 3/2011 | Bailey et al. |
| 2011/0091977 A1 | 4/2011 | Kilian et al. |
| 2012/0107801 A1 | 5/2012 | Kilian et al. |
| 2012/0190115 A1 | 7/2012 | Kilian et al. |
| 2012/0208279 A1 | 8/2012 | Vick et al. |
| 2012/0277417 A1 | 11/2012 | Kilian et al. |
| 2012/0277418 A1 | 11/2012 | Kilian et al. |
| 2013/0078716 A1 | 3/2013 | Vick et al. |
| 2013/0102040 A1 | 4/2013 | Radakovits et al. |
| 2013/0131330 A1 | 5/2013 | Kilian et al. |
| 2013/0281683 A1 | 10/2013 | Kilian et al. |
| 2013/0295665 A1 | 11/2013 | Kilian et al. |

FOREIGN PATENT DOCUMENTS

| | | |
|---|---|---|
| IN | 31/2013 A1 | 8/2013 |
| IN | 37/2013 A1 | 9/2013 |
| MX | 20110000934 A1 | 7/2011 |
| WO | 2004106238 A2 | 12/2004 |
| WO | 2007084078 A1 | 7/2007 |
| WO | 2008060571 A8 | 5/2008 |
| WO | 2008106803 A1 | 9/2008 |
| WO | 2009124070 A1 | 10/2009 |
| WO | 2009149465 A1 | 12/2009 |
| WO | 2009149470 A1 | 12/2009 |
| WO | 2010011335 A1 | 1/2010 |
| WO | 2010147662 A1 | 12/2010 |
| WO | 2011011463 A2 | 1/2011 |
| WO | 2011049995 A1 | 4/2011 |
| WO | 2012149457 A1 | 11/2012 |
| WO | 2013166065 A1 | 11/2013 |

OTHER PUBLICATIONS

Office Action mailed Nov. 14, 2012 in China Patent Application No. 200980138072.X, filed Jul. 24, 2009.
Official Action mailed Jul. 10, 2012 in Mexico Patent Application No. MX/a/2011/000934, filed Jul. 24, 2009.
Official Action mailed Mar. 5, 2013 in Mexico Patent Application No. MX/a/2011/000934, filed Jul. 24, 2009.
Duarte et al., "Glyphosate (GP) Effects with Emphasis on Aquatic Organisms," Columbia Orinoquia, ISSN: 0121-3709, pp. 70-100, 2004.
Technical Card: Glyphosate, Document filed for the Pesticide Action Network and the Alternatives Thereof, for Latin America (RAP-AL)-Communications and Administration Office, Apr. 2008.
Republic of Columbia Department of Environment, Housing and Territorial Development, Resolution (1009), published Jun. 17, 2008. (36 pages).
International Search Report and Written Opinion of the International Searching Authority mailed Oct. 30, 2009 for Application No. PCT/US2009/046656, filed Jun. 8, 2009.
International Search Report and Written Opinion of the International Searching Authority mailed Aug. 12, 2009 for Application No. PCT/US2009/003819, filed Jun. 25 2009.
International Search Report and Written Opinion of the International Searching Authority mailed Dec. 20, 2010 for Application No. PCT/US2010/053265, filed Oct. 19, 2010.
Extended European Search Report mailed Mar. 19, 2013 in European Patent Application 10825551.4, filed on Oct. 19, 2010.
Minoda et al., "Improvement of Culture Conditions and Evidence for Nuclear Transformation by Homologous Recombination in a Red Alga, *Cyanidioschyzon merolae* 10D," Plant and Cell Physiology, vol. 45, No. 6, Jun. 2004, pp. 667-671.
Hallmann et al., "Gene Replacement by Homologous Recombination in the Multicellular Green Alga, *Volvox carteri*," Proceedings of the National Academy of Sciences in the United States of America, vol. 94, No. 14, 1997, pp. 7469-7474.
Kilian et al., "High-efficiency homologous recombination in the oil-producing alga *Nannochloropsis* sp.," Proceedings of the National Academy of Sciences of the United States of America, vol. 108, No. 52, Dec. 2001, pp. 21265-21269.
Extended European Search Report mailed Oct. 19, 2011 in European Patent Application 09759628.2, filed on Jun. 8, 2009.
Hallmann, "Algal Transgenics and Biotechnology," Transgenic Plant Journal, Global Science Books Ltd., GB, vol. 1, No. 1, Jan. 2007, pp. 81-98.
International Search Report and Written Opinion of the International Searching Authority mailed Oct. 20, 2010 for Application No. PCT/US2010/001754, filed Jun. 16, 2010.
International Search Report and Written Opinion of the International Searching Authority mailed Sep. 9, 2009 for Application No. PCT/US2009/046650, filed Jun. 8, 2009.
International Search Report and Written Opinion of the International Searching Authority mailed Jun. 15, 2011 for Application No. PCT/US2010/042666, filed Jul. 20, 2010.
Pollock, "High Carbon Dioxide Requiring Mutants of *Chlamydomonas reinhardtII*," Created Dec. 2003, [online, retrieved Oct. 14, 2010] <http://etd.Isu.edu/docs/available/etd-0828103-114026/unrestricted/Pollock_dis.pdf>.
Drocourt: GenBank Accession No. X52869.1, created Jan. 3, 1995.
Pan: GenBank Accession No. EE109892.1, created Jun. 23, 2008.
Pan: GenBank Accession No. EE109907, created Jun. 23, 2008.
Henriquez et al.: GenBank Accession No. Q07CY9, created Oct. 31, 2006.
International Search Report and Written Opinion of the International Searching Authority mailed Oct. 16, 2012 for Application No. PCT/US2012/035633, filed Apr. 27, 2012.
Yu et al., "Construction and characterization of a normalized cDNA library of *Nannochloropsis oculata* (Eustigmatophyceae)," Chinese Journal of Oceanology and Limnology, vol. 28, No. 4, pp. 802-807, 2010.
Lumbreras et al., "Efficient Foreign Gene Expression in *Chlamydomonas reinhardtii* Mediated by an Endogenous Intron," The Plant Journal, vol. 14, No. 4 Jan. 1, 1998, pp. 441-447, XP001150496, ISN: 0960-7412, DOI: 10.1046/j.1365-313X.1998.00145.X.
Rose A.B., "Intron-Mediated Regulation of Gene Expression," Current Topics in Microbiology and Immunology vol. 326, Jan. 1, 2008, pp. 277-290, XP009145370, ISSN: 0070-217X.
Rose A.B., "The Effect of Intron Location on Intron-Mediated Enhancement of Gene Expression in *Arabidopsis*," The Plant Journal, vol. 40, No. 5, Dec. 1, 2004, pp. 744-751, XP55029911, ISSN: 0960-7412, DOI:10.1111/j.1365-313X.2004.02247.
International Search Report and Written Opinion of the International Searching Authority mailed Sep. 13, 2013 in Application No. PCT/US2013/038939 filed Apr. 30, 2013.
Notice on the First Office Action mailed May 20, 2013 in Chinese Application No. 201080058106.7 filed Oct. 19, 2010.

(56) References Cited

OTHER PUBLICATIONS

Examination Report mailed Feb. 20, 2013 in Australian Application No. 2009274500 filed Jul. 24, 2009.
Examination Report mailed Apr. 29, 2013 in European Application No. 09759628.2 filed Jun. 8, 2009.
Examination Report mailed Aug. 29, 2013 in Australian Application No. 2009255947 filed Jun. 8, 2009.
Examination Report mailed Sep. 19, 2013 in Australian Application No. 2010310765 filed Oct. 19, 2010.
Notice on the Second Office Action mailed Sep. 24, 2013 in Chinese Application No. 200980138072.X filed Jul. 24, 2009.
Ruan, Zuo-xi et al., Effects of Acute Glyphosate Exposure on the Growth and Physiology of *Nostoc sphaeroides*, an Edible Cyanobacterium of Paddy Rice Fields, Acta Hydrobiologica Sinica, Jul. 2008 vol. 32, No. 4, pp. 462-468.
Office Action mailed Nov. 11, 2013 in Mexican Application No. MX/a/2011/000934 filed Jul. 24, 2009.
Office Action mailed Feb. 7, 2014 in Chinese Application No. 201080058106.7 filed Oct. 19, 2010.
Office Action mailed Mar. 5, 2014 in European Application No. 10825551.4 filed Oct. 19, 2010.
Office Action mailed Mar. 27, 2014 in Israeli Application No. 210805 filed Jul. 24, 2009.
Office Action mailed May 26, 2014 in Mexican Application No. MX/a/2012/004579 filed Oct. 19, 2010.
Office Action mailed Jun. 12, 2014 in Chinese Application No. 200980138072.X filed Mar. 24, 2011.
Summons to Attend Oral Proceedings mailed Jun. 17, 2014 for European Application No. 09759628.2, filed May 5, 2011.
Office Action mailed Jul. 16, 2014 in European Application No. 10825551.4 filed Oct. 19, 2010.
Office Action mailed Jul. 14, 2014 in Mexican Application No. MX/a/2011/000934 filed Jul. 24, 2009.
Office Action mailed Sep. 11, 2014 in Israeli Application No. 210805 filed Jul. 24, 2009.
Lembi et al. (2009). Identifying and Managing Aquatic Vegetation. Aquatic Plant Management. https://www.extension.purdue.edu/extmedia/APM/APM_3_W.pdf.
Office Action, Dec. 2, 2010, U.S. Appl. No. 12/220,688, filed Jul. 24, 2008.
Final Office Action, Jul. 12, 2011, U.S. Appl. No. 12/220,688, filed Jul. 24, 2008.
Advisory Action, Sep. 23, 2011, U.S. Appl. No. 12/220,688, filed Jul. 24, 2008.
Office Action, Apr. 2, 2014, U.S. Appl. No. 12/220,688, filed Jul. 24, 2008.
Office Action, Jul. 22, 2011, U.S. Appl. No. 12/480,635, filed Jun. 8, 2009.
Final Office Action, Jan. 31, 2012, U.S. Appl. No. 12/480,635, filed Jun. 8, 2009.
Final Office Action, Apr. 6, 2012, U.S. Appl. No. 12/480,635, filed Jun. 8, 2009.
Notice of Allowance, Jul. 19, 2012, U.S. Appl. No. 12/480,635, filed Jun. 8, 2009.
Notice of Allowance, Aug. 27, 2012, U.S. Appl. No. 12/480,635, filed Jun. 8, 2009.
Office Action, Feb. 9, 2012, U.S. Appl. No. 12/492,077, filed Jun. 25, 2009.
Final Office Action, Oct. 9, 2012, U.S. Appl. No. 12/492,077, filed Jun. 25, 2009.
Office Action, Aug. 29, 2011, U.S. Appl. No. 12/706,683, filed Feb. 16, 2010.
Final Office Action, May 2, 2012, U.S. Appl. No. 12/706,683, filed Feb. 16, 2010.
Notice of Allowance, Jul. 13, 2012, U.S. Appl. No. 12/706,683, filed Feb. 16, 2010.
Office Action, Dec. 10, 2010, U.S. Appl. No. 12/581,812, filed Oct. 19, 2009.
Final Office Action, Jun. 3, 2011, U.S. Appl. No. 12/581,812, filed Oct. 19, 2009.
Office Action, Apr. 5, 2013, U.S. Appl. No. 12/581,812, filed Oct. 19, 2009.
Notice of Allowance, Jul. 3, 2014, U.S. Appl. No. 12/581,812, filed Oct. 19, 2009.
Office Action, May 23, 2012, U.S. Appl. No. 12/488,106, filed Jun. 19, 2009.
Final Office Action, Mar. 14, 2013, U.S. Appl. No. 12/488,106, filed Jun. 19, 2009.
Office Action, Dec. 29, 2010, U.S. Appl. No. 12/488,611, filed Jun. 8, 2009.
Notice of Allowance, Jul. 22, 2011, U.S. Appl. No. 12/488,611, filed Jun. 8, 2009.
Notice of Allowance, Oct. 18, 2011, U.S. Appl. No. 12/488,611, filed Jun. 8, 2009.
Office Action, Jan. 30, 2013, U.S. Appl. No. 13/011,809, filed Jan. 21, 2011.
Notice of Allowance, Aug. 23, 2013, U.S. Appl. No. 13/011,809, filed Jan. 21, 2011.
Notice of Allowance, Dec. 24, 2013, U.S. Appl. No. 13/011,809, filed Jan. 21, 2011.
Office Action, Jun. 14, 2012, U.S. Appl. No. 12/840,269, filed Jul. 20, 2010.
Final Office Action, Jan. 25, 2013, U.S. Appl. No. 12/840,269, filed Jul. 20, 2010.
Notice of Allowance, Aug. 6, 2013, U.S. Appl. No. 12/840,269, filed Jul. 20, 2010.
Notice of Allowance, Dec. 13, 2013, U.S. Appl. No. 12/840,269, filed Jul. 20, 2010.
Notice of Allowance, Oct. 3, 2012, U.S. Appl. No. 13/458,914, filed Apr. 27, 2012.
Notice of Allowance, Jan. 14, 2013, U.S. Appl. No. 13/458,914, filed Apr. 27, 2012.
Office Action, Jul. 10, 2013, U.S. Appl. No. 13/459,215, filed Apr. 29, 2012.
Notice of Allowance, Apr. 10, 2014, U.S. Appl. No. 13/459,215, filed Apr. 29, 2012.
Office Action, Jul. 23, 2012, U.S. Appl. No. 13/372,467, filed Feb. 13, 2012.
Final Office Action, Mar. 13, 2013, U.S. Appl. No. 13/372,467, filed Feb. 13, 2012.
Notice of Allowance, Feb. 14, 2014, U.S. Appl. No. 13/372,467, filed Feb. 13, 2012.
Notice of Allowance, Apr. 29, 2013, U.S. Appl. No. 13/685,659, filed Nov. 26, 2012.
Notice of Allowance, Aug. 2, 2013, U.S. Appl. No. 13/685,659, filed Nov. 26, 2012.
Notice of Allowance, Nov. 7, 2013, U.S. Appl. No. 13/685,659, filed Nov. 26, 2012.
Notice of Allowance, Jul. 29, 2013, U.S. Appl. No. 13/888,310, filed May 6, 2013.
Notice of Allowance, Nov. 26, 2013, U.S. Appl. No. 13/888,310, filed May 6, 2013.
Notice of Allowance, Mar. 7, 2014, U.S. Appl. No. 13/888,310, filed May 6, 2013.
Notice of Allowance, Oct. 18, 2013, U.S. Appl. No. 13/915,555, filed Jun. 11, 2013.
Notice of Allowance, Jan. 31, 2014, U.S. Appl. No. 13/915,555, filed Jun. 11, 2013.
Office Action, Feb. 21, 2014, U.S. Appl. No. 13/246,700, filed Sep. 27, 2011.
Santin-Montanya, et al. "Optimal Growth of *Dunaliella primolecta* in Axenic Conditions to Assay Herbicides," Chemosphere, 66, Elsevier 2006, p. 1315-1322.
Felix, R. "Use of the cell wall-less alga *Dunaliella bioculata* in herbicide screening tests," Annals of Applied Biology, 113, 1988, pp. 55-60.
Janssen, M. et al. "Phytosynthetic efficiency of *Dunaliella tertiolecta* under short light/dark cycles," Enzyme and Microbial Technology, 29, 2001, p. 298-305.
Saenz, M.E., "Effects of Technical Grade and a Commercial Formulation of Glyphosate on Algal Population Growth," Bulletin of Environmental Contamination Toxicology, 1997, 59: pates 638-644.

(56) References Cited

OTHER PUBLICATIONS

Christy et al., "Effects of Glyphosate on Growth of *Chlorella*," Weed Science, vol. 29, Issue 1, Jan. 1981, pp. 5-7.
Roessler et al., "Genetic Engineering Approaches for Enhanced Production of Biodiesel Fuel from Microalgae," ACS Symposium Series; American Chemical Society, 1994, pp. 255-270.
Endo et al. "Inactivation of Blasticidin S by *Bacillus cereus* II. Isolation and Characterization of a Plasmid, pBSR 8, from *Bacillus cereus*," The Journal of Antibiotics 41 (2): 271-2589-2601, 1988.
Hallmann et al., "Genetic Engineering of the Multicellular Green Alga Volvox: A Modified and Multiplied Bacterial Antibiotic Resistance Gene as a Dominant Selectable Marker" The Plant Journal 17(1): 99-109 (Jan. 1999).
Kindle et al., "Stable Nuclear Transformation of *Chlamydomonas* Using the *Chlamydomonas* Gene for Nitrate Reductase" The Journal of Cell Biology 109 (6, part 1) 1989: 2589-2601.
Prein et al. "A Novel Strategy for Constructing N-Terminal Chromosomal Fusions to Green Fluorescent Protein in the Yeast *Saccharomyces cerevisiae*" FEBS Letters 485 (2000) 29-34.
Schiedlmeier et al., "Nuclear Transformation of *Volvox Carteri*" Proceedings of the National Academy of Sciences USA 91(11): 5080-5084 (May 1994).
Wendland et al. "PCR-Based Methods Facilitate Targeted Gene Manipulations and Cloning Procedures" Curr.Gen. (2003) 44:115-123.
Molnar et al., "Highly Specific Gene Silencing by Artificial MicroRNAs in the Unicellular Agla *Chlamydomonas reinhardtii*," Plant Jour. ePub Jan. 17, 2009, vol. 58, No. 1, pp. 157-164 (Abstract Only).
Chen et al., "Conditional Production of a Functional Fish Growth Hormone in the Transgenic Line of *Nannochloropsis oculata* (Eustigmatophyceae)," J. Phycol. Jun. 2008, vol. 44, No. 3, pp. 768-776.
Nelson et al., "Targeted Disruption of NIT8 Gene in *Chlamydomonas reinhardtii*." Mol. Cell. Bio. Oct. 1995, vol. 15, No. 10, pp. 5762-5769.
Kureshy et al., "Effect of Ozone Treatment on Cultures of *Nannochloropsis oculata*, *Isochrysis galbana*, and *Chaetoceros gracilis*," Journal of the World Aquaculture Society, 1999, 30(4), pp. 473-480.
Genbank Accession No. U71602 (*Nannochloropsis* sp. Violaxanthing/chlorophyll a binding protein precursor (NANVCP) mRNA, 1998.
Sukenik et al. "Characterization of a Gene Encoding the Light-Harvesting Violaxanthin-Chlorophyll Protein of *Nannochloropsis* Sp. (Eustigmatophyceae)," Journal of Phycology, Jun. 2000; 36(3), pp. 563-570.
Abe et al., AG610981, Musmusculus molossinus DNA, 2004.
Kopczynski et al., CO268749, *Drosophila melanogaster* cDNA clone EK092604, 2004.
Csogor et al., "Light Distribution in a Novel Photobioreactor-Modelling for Optimization," Journal of Applied Phycology, vol. 13, 2001, pp. 325-333.
Janssen et al., "Enclosed Outdoor Photobioreactors: Light Regime, Photosynthetic Efficiency, Scale-Up, and Future Prospects," Biotechnology and Bioengineering, vol. 81, No. 2, pp. 193-210, Jan. 2003.
Zittelli et al., "Mass Cultivation of *Nannochloropsis* Sp. In Annular Reactors," Journal of Applied Phycology, vol. 15, pp. 107-113, Mar. 2003.
Strzepek et al., "Photosynthetic Architecture Differs in Coastal and Oceanic Diatoms," Nature, vol. 431, pp. 689-692, Oct. 2004.
Shi et al., "Analysis of Expressed Sequence Tags from the Marine Microalga *Nannochloropsis oculata* (eustigmatophyceae)," Journal of Phycol, vol. 44, pp. 99-102, 2008.
Thiel et al., "Transformation of a Filamentous Cyanobacterium by Electroporation," Journal of Bacteriology, Oct. 1989, vol. 171, No. 10, pp. 5743-5746.
Krienitz et al., "*Nannochloropsis limnetica* (Eustigmatophyceae), a new species of picoplankton from freshwater," Phycologia, 2000, vol. 39, No. 3, Abstract (ful article pp. 219-227).
Lee et al., "Isolation and Characterization of a Xanthophyll Aberrant Mutant of the Green Alga *Nannochloropsis oculata*," Marine Biotechnology, 2006, vol. 8, pp. 238-245.
Sukenik et al., "Regulation of Fatty Acid Composition by Irradiance Level in the Eustigmatophyte *Nannochloropsis*," Journal of Phycol., 1989, vol. 25, pp. 686-692.
Rocha et al., "Growth Aspects of the Marine Microalga *Nannochlorpsis gaditana*," Biomolecular Engineering, 2003, vol. 20, pp. 237-242.
MacIntyre et al., "Primary Production by Suspended and Benthic Microalgae in a Turbid Estuary: Time-Scales of Variability in San Antonio Bay, Texas," Marine Ecology Progress Series, 1996, vol. 145, pp. 245-268.
Dunahay et al, "Manipulation of Microalgal Lipid Production Using Genetic Engineering," Applied Biochemistry and Biotechnology, 1996, vol. 57/58, pp. 223-231.
Witkowski et al., "Conversion of a B-Ketoacyl Synthase to a Malonyl Decarboxylase by Replacement of the ActiveSite Cysteine with Glutamine," Biochemistry, 1999, vol. 38, 11643-11650.
Kisselev, "Polypeptide Release Factors in Prokaryotes and Eukaryotes: Same Function, Different Structure," Structure, vol. 10, Jan. 2002, pp. 8-9.
Whisstock et al., "Predication of protein function from protein sequence and structure," Q. Rev. Biophysics, 2003, vol. 36, pp. 307-340.
Broun et al., "Catalytic Plasticity of Fatty Acid Modification Enzymes Underlying Chemical Diversity of Plant Lipids," Science, vol. 282, 1998, pp. 1315-1317.
Wishart et al., "A Single Mutation Converts a Novel Phosphotyrosine Binding Domain into a Dual-specificity Phosphatase," J. Biol. Chem. 1995, vol. 270(45), pp. 26782-26785.
Geng et al, "Construction of a System for the Stable Expression of Foreign Genes in *Dunaliella salina*," Acta Botanica Sinica 46(3): 342-346, 2004.
Chen et al., "Highly Efficient Expression of Rabbit Neutrophil Peptide-1 gene in *Chlorella* Ellipsoidea Cells," Current Genetics 39(5-6): 365-370, 2001.
Suga et al., "Control by Osmolarity and Electric Field Strength of Electro-Induced Gene Transfer and Protein Release in Fission Yeast Cells," Journal of Electrostatics 64(12): 796-801, 2006.

\* cited by examiner

P525
(underlined)

→ ACCGAGTGAAGCAACGCCAGAGCTATGGACAAGGAATCCAAGGAGATAACTGTATTTCAC
GCACCTTCTTTGACCTCCTTCTCTCAACCCCCAACATTTCGCATGCCCATTCGGTCATAA
TCCTGTGGGCTCGCTGCTCTCGCCTTTGCTGCCTCCGCGTCGACGCATCCAGTCCTTCCG
TCCCTGCTCTATTCACACGTCTACAATTTTCCATATGCATGAGTTGCAATCTTTGCCCTC
TCTGTTCTCACCATGTCTCCTGCCATGGCCCCACGTCTTGCGTCGGGGCTGTGGCGTTTT
GAGAATGGGTGACAGGGAAGCGAACACAGGCTAAGGGAGACGCATGCGTCGGCGGGTCTC
GACACTCCACGCCTTGTCGGCAGAAAGGCGACGCACGAGCCAAAAAGCACTAGAAGGCCT
TTTCTTGGGCATCTTTTCTCTGTACGGCCCCTTATCAGCCTGTCTTATTGTGCTGGTGTT
GCTTGCGTGCGCCCTTGACATCGATTACTCCGGGAGGCTGCGCGGCCGTTGCTTTGGTCA
ACGTCGACACGACACCTCTCCCCAACATGCACGGCAGAGTGATCTTCGGGTGTGATGTTG
CGTGAACGGCCTTTGTGCCACTTCTTTCACCGGCCCAACCATACCCGCATCCACTCGCAA
GCTTATAGACCTTATATCAGGCTTCGATACTCTGCGACCATGCTTCGCACCGGGCTCGGC
AGAGACGTGGTGAAAGCCGAGCCTTAGCTTGCTTCGCGTCCTATGATGATTCCACCACCA
TTGCCTACACGACACGATACACCCGTACACGCCCATGCTACACCCTGCCTACACACGCGC
ACACGCGCACAAACACACACATACATCAACACACACAATACAGCAATCCGTGCCTCTCTC
TTACTCTATTCAAGCGTGCTGCGTGGCCTTTGACTTCATTCCTCTTGTCCACCCGCCGGC
CACCAGTAGAACCAGCACCACGTCCACCCTCATCTCACTCCTCTTTCCCCCACATCCCCT

P526 (revrs)
(underlined)

→ ACTACTCCATCCTTCTCATCTACAGTCACACCTTCCTCCTCTTCACTTAACCATGCGTGT ← ATG =
CCTTGCTTTCTTCGCCCTCCTGGCCGCACCCGCCCTGGCCTTCGTGCCCCGTATGCCCGC  start
CCCCGTGCGTGCCCGCGCCAGTCTCACCCTCCGATTCTCTGGAGAGTACAGCGAGAAG    codon
                                                               ACP
                                                               gene Intron I (entire
underlined)

→ <u>GTAAGCCACCTCTCTTTCCTTCATGTCCTATCTTGCGCCCTCCTTCCCCATGCTTCTTCCCC
GATATTTTGTGGTCAGTTCTTGGTGTGTCACCTTGGGGTGGGCGGGTGAACCGCAGCGAT
TTCTCTTTCAGGGATGTGGGGGCTGGATGCCCGTCTTGGCTACCTTTCCCTTCCCTCCCT
GGTCCCGTCCCTTCTCCTCCCTTTTCACTTCTCTCTCTTTTTTTTCTTCCTCTCCCCCTC
CTCGAACTTCCCCTGGCCGAAAGTGATCCATGTCCCACTTTCACTTACCCGCCCTCCCTC
CCTCCCTCCCCCTCTCCCTCCAG</u>

FIG. 5 (SEQ ID NO:1)

Intron II (entire underlined)

TAA = stop codon ACP gene

```
GTGCGCGCCATCGTGTTGGAGAACATGGGCGATGATG
CCAAGGTGCAGGACTACCTGAAGGCCAACGGTGATGATAAGGCCGAGTTCGCCGCCATGG
GCTTTGATTCTTTGGACTTGGTGGAGTTCTCCATGGCCATCCAGAAG

GTACGGGAACCTGCCTTCCTTCTCTCCCTCCCTCCCAACCTACTTCCCTTCCATCACGGC
GCCGAGCTCTCTG
TCTCCGATCTCATGGGTATATCGTTGTGTCTGCCTCGTCGAGCCCGTAGTTTAGACATCG
ATATCATTCTCATGCACTCCATCAAATGAAAATTAATATTAATTTTCCACTCACATACTC
TCCCCTCCCTTCCTTCCTCTCTTCTCAG

GAGTTCGACCTCCCGGACCTGAACGAGGAGGA
CTTCGCCAACCTCAAGACGATCAAGGACGTGGTCACTATGGTGGAGGCCAACAAGAAG
TAA
ACACACAACGGCAGCGACAGCAGCAGCACCAGCAGCATGCACGAGGGGAGGAGGAAGAT
GACTCGGTTGTTGGTTGGTGTGTTGACGTATTGTGATATGTGTGCATTCTCACCCTAATT
GGTCTTCACATCTCCTCTCGTCTCCCTTTCCTGGGAAGGGATGGCGGGAAGGAAAGAGGG
AGGGAGTGCTTGTGTGTGCTATGTTGTGTTTCGTGTGGCATGACTGGAGGTGGGCGATTA
ACAGCAAGAGGAGAAATTGGGCTGAATGAACGCTTAAGTCGTGTCTGTGTTTGTGACGAT
GAGTGGGGAGGACGTAGCCTCATCCCCCTTTTCTTCCCGGTCGGTCTTTTTCGGCCTTTT
CCTCCTTCCCCTCCAAGGGTGGAAGGAGGAGGATGGACAGGGCGAGAGACAAGAGAAGGA
TGGGGCTAGAGAATCCACACACAACTAGAGATAGAAGTACTTTATCCTTGTTCTCCTTCT
TGTTATTGACGTGTTGATTTTTGGTCCTCTTCTTGCGCGCGATCTTTCTCTCGTTCGTCG
ATCTTTCGTCTTTTTTTCTTTTGTCAACTCTCTCTCTCTTCACCGACGCCTCTTCGAAGA
ATCTATTTCCTCTCTACTTCTGCCCTCTCGTGTCTTAAATTTAATCCTCGCGGTTTTCGT
CTTCTCTCCCTCCACCACCAATCCCTTCTCCTTTCTCGTCCCCTTCCACATCCCCCCCAC
CCCCTCCTCCTAAACCTGTTTCACTGTGGCCCTCCGCGATGAAGATGCCCGATTGGTGCG
TGCCCTGTCATATGTACGCATATATCTATAATTGTTTATACATATTTAAATTCTTTCCTT
CCCTTCTCAAGCCCCTGTGGCTTTGTCTCTATTCGTCTCCTTCTGCCCGCCTCCGCGTTC
CTTCCCCCCCCCTCCCTCACGGCCTCCCTCCTCACCTCGGGTGCCTGCGTCTCCTGCCCT
CGATCGAACCGCGCAGTGAATTCAGTTGTCACACGAGGATGTTCGCCTGGGGCCGTGGGG
T
```

FIG. 5 (SEQ ID NO:1)(Continued)

ACAGTCACACCTTCCTCCTCTTCACTTAACCATGCGTGTCCTTGCTTTCTTCGCCCTCCTGGCCGCACCCGCCCTGGCCTTCGTGCCCCG
TATGCCCGCCCCGTGCCGTGCCCTGCCCAGTCTCACCCTCGATTCTCTGGAGAGTACAGCGAGAAGGTGCGCGCCATCGTGTTGGAGAA
CATGGGCGATGATGCCAAGGTGCAGGACTACCTGAAGGCCAACGGTGATGATAAGGCCGAGTTCGCCGCCATGGGCTTTGATTCTTTGA
CTTGGTGGAGTTCTCCATGGCCATCCAGGAGTTCGACCTCCCGGACCTGAAGGAGGACTTCGCCAACCTCAAGACGATCAAGGA
CGTGGTCACTATGGTGGAGGCCAACAAGAAGTAAACACACAACGGCAGCAGCGACAGCATGCACCAGCAGGGGAGGAGGAA
GATGACTCGGTTGTTGGTTGGTGTGTTGACGTATTGTGATATGTGTCATTCTCACCCTAATTGGTCTTCACATTCTCCTCGTCTCCCT
TTCCTGGGAAGGGGATGGCGCGGAAGGAAAAGAGGAGGGAGGGAGGAGTGCTTGTGTGTGCTATGTGTTGTGTTTCGTGTGGCATGACTGGAGG

FIG. 6 (SEQ ID NO:2)

P525 (underlined) →

<u>TGTTCTCACCATGTCTCTGCCATGGGCCCACGTCTTTGCGTCGGGGCTGTGGCGTTTTGAGAATGGGTGACAGGGAAGGGAACACAGGCTAAGGGAGAC</u>
GCATGCGTCGGGGGTCTCGACACTCCACGCCTTGTCGGCAGAAAGGCGACGAGCCAAAAGCCCTTTTCTTGGGCATCTTTCTC
TGTACGGCCCCTTATCAGCCTGTCTTATTGTGCTGGTGTTGCTTGCGTGCGCCTTGACATCGATTACTCCGGGAGGCTGCGCCGTTGCTTGGTCAA
CGTCGACACGACACACTCTCCCCAACATGCACGGCAGAGTGATCTTCGGGTGTGATGTTGCGTGAACGGCCTTTGCCACTTCTTCACCGGCCAACCA
TACCCGCATCCACTCGCAAGCTTATAGACCTTATATCAGGCTTCGACCATGCTTCGATACTCTGGACACGATACACCCTGCCAGAGACGTGGTGAAAGCGA
GCCTTAGCTTGCTTCGCGTCCTATGATGATTCCACCACCATTGCCTACACGACACCCGTACACGCCCATGCTACACCCTGCCTACACACGCGCA
CACGCGCACAAACACACACATATACATTCAACACACAGCAATACAGACCGTGCTCTCTCTTATTCAAGCGTGCTGGCCTTTGACTTCATTCC
TCTTGTCCACCGGCCACCAGTAGAACCAGCACCACGTCCACCCTCATCTCACTCCTTCCCCCACATCCCTACTCCTCCATCCTTCTCATCT acagtcacacttctctcttcacttaaccATGGCCAAGTTGACCAGTGCCGT ← P526 (underlined)

FIG. 7 (SEQ ID NO:3)

ATG =
start
codon *sh*
*ble* gene

P113 (entire underlined)

TAA = stop codon *sh ble* gene

ATGGCCAAGTTGACCAGTGCCGTTCCGGTTGCCTCACCGGCGCCGACGTCGCCGAGCGGTCGAGTTCTGACCGGCTCGGGTT
CTCCCGGGACTTCGTGGAGGACGACTTCGCCGGTGTGGTCCGGGACGACGTGACCCTGTTCATCAGCGCGTCGACCAGGTGG
TGCCGGACAACACCCTGGCTGGGTGTGGGCGCGGCCTGACGACGAGCTGTACGCCGAGTCGTGTCCACGAACTTC
CGGGACGCCTCCGGGCCCATGACCGAGATCGGCGAGCAGCCGTGGGGCGGAGTTCGCCCTGCGACCCGGCAACTG
CGTGCACTTCGTGGCCGAGGAGGACTAA

GCTTCTGTGTGGAAGAGCCAGTGGTAGTAGCAGTAGCAGCAGCCGCAGCAGCCGCAGCACTCAGTGTTGGCGCGAG
AGATTGTCCATCCCTTCTTAAGCTACCGGAAGAGAAATAAGGCCCTTTCTCCCGTAGCTGTCTTCGTTGTTTGT
GCTGATTGCTTGATATGAGAGTGTTGAATTCCTGCATCATGTTTTTCTCGTAGTCCTTTCCTACCCCCGTCAT
TTTCTTTTCTCCCCTGGTTCTCTTTCGCTCCCCCTTTATTTCACCCCTTATTTCTTTGTTTATAGTGAGAGGAAG
*GTAGAGAGGGGAAAACAAGAACAACGAACGCAAGCCGTGTGAA*

P266 (underlined)

UTR of NT7
Transformation
construct, partially
(larger font in
*italics*)

FIG. 8 (SEQ ID NO:4)

P525 (entire underlined)　　　ACP Promoter (larger standard font)

TGTTCTCACCATGTCTCCTGCCATGGCCCCACGTCTCTTGCGTCGGGGCTGTGGCGTTTTGAGAATGGG
TGACAGGGAAGCGAACACAGGCTAAGGGAGACGCATGCGTCGGCGGGTCTCGACACTCCACGC
CTTGTCGGCAGAAAGGCGACGCACGAGCCAAAAAGCACTAGAAGGCCTTTTCTTGGGCATCTT
TTCTCTGTACGGCCCCCTTATCAGCCTGTCTTATTGTGTGCGTGTGTTGCGTGCGCCCTTGA
CATCGATTACTCCGGGAGGCTGCGCGGCCGTTGCTTTGGTCAACGTCGACACGACACCTCTCC
CCAACATGCACGGCAGAGTGATCTTCGGGTGTGATGTTGCGTGAACGCCTTTGTGCCACTTC
TTTCACCGGCCCAACCATACCCGCATCCACTCGCAAGCTTATAGACCTTATATCAGGCTTCGA
TACTCTGCGACCATGCTTCGCACCGGCTCGGCAGAGACGTTGTGAAAGCCGAGCCTTAGCTT
GCTTCGCGCTTCCTATGATGATTCCACCACCATTGCCTACACGACACGATACACCCGTACACGCC
CATGCTACACCCTGCCTACACGCGCACAAACACACACATACATACATCAACACACAC
AATACAGCAATCCGTGCCTCTCTCTATTCAAGCGTGCTGCGTGCCTTTGACTTCAT
TCCTCTTGTCACCCGCCGGCCACCAGTAGAACCAGCACCACGTCCACCCTCATCTCACTCCT
CTTTCCCCCACATCCCCTACTACTCCATCCTTCTCATCTACAGTCACACCTTCCCTCCTTCA
CTTAACC

P113 (entire underlined)

ATGGCCAAGTTGACCAGTGCCGTTCCGGTGCTCACCGCGCCGGAGCGTCGAGTTCTGGACCGA

ATG = start codon sh ble gene

CCGGCTCGGGTTCTCCCGGACCAGGTCGTGTGGAGGACGACTTCGCCGGTCCGGACGACGTGACCCTGTTCA
TACGCCGAGTGGTCGGAGGTCGTGTCCACGAACTTCCCGGACGCCTCCGGGACGCCATGACCGAGATCGGCGA
GCAGCCGTGGGGCGGGAGTTCGCCCTGCGCCGGCCAACTGCTGCACTTCGTGCCGAGGAGCAGG
ACTAA

UTR of NT7 Transformation construct, partially (larger font in italics)

GCTTCTCGTGGAAGAGCCAGTGGTAGTAGCAGTGGTAGCAGCCGCAGCACTCAGT
GTTGGCGCGAGAGATTGTCCATCCCTTCTTAACCTACCGGAAGAGAGAAATAAGGCCTTTCTCCC
GTAGCTGTCTTCGTTTGTTTGTGCTTGATATGAGAGTGTTGAATTCCTGCATCATG
TTTTTCTCTGTAGTCCTTTCATTTTCTTTTTGTTTATAGTGAGAGGAAGGTAGAGAGGGAAAAACAAGA

P266 (underlined)

ACAACGAACGCAAGCGTGTGAA

FIG. 9 (SEQ ID NO:5)

P563 (entire underlined)

GAACAACGAAGCAAGCGTGTGAATGTTCTCACCATGTCTCCTGCCAT
GGCCCCACGTCTTGCGTCGGGCGTGTGGCGTTTGAGAATGGGTGACAGGGAAGCGAACACAGGCTAAGGGAGACGCATGCGTCGGCGGGTC
TCGACACTCCACGCCTTGTCGCAGAAAGGCGACGCAGAGCCAAAAGCACTAGAAGGCCTTTCTTTGGGCATCTTTTCTCTGTACGGCCCCTT
ATCAGCCTGTCTTATTGTGCTGGTGTTGCTTGCGCTGCGCCCTTGACATCGATTACTCCGGAGGCTGCGCGGCCGTTGCTTTGGTCAACGTCGAC
ACGACACCTCTCCCCAACATGCAGGCAGAGTGATCTTCGGGTGTGATGTTGCGTGAACGGCCTTTGTGCCACTTCTTCACCGGCCAACCATA
CCCGCATCCACTGCCAAGCTTATAGACCTTATCAGGCTTCGATACTCTGCGACCATGCTTCGCACGGGCTCGGCAGAGACGTGGTGAAAGC
CGAGCCTTAGCTTGCTTGCGTCCTATGATGATTCCACCACCATTGCCTACACGACACGATACACCCGTACAGCCCATGCTACACCCTGCCTACA
CACGCGCACACGGCACAAACACATCAACATACAACACACAATACAGCAATCCGTGCCTCTCTTACTCTATTCAAGCGTGCTGCGTGGCC
TTTGACTTCATTCCTCTTGTCACCCGCCGGCCACCGCACCACCAGCAGTAGAACCAGCACCACGTCCACCCTCCACTCCTCCTTCCCCACATCCCCTACTACT
CCATCCTTCTCATCT

ACAGTCACACCTTCCTCCTCTTCACTTAACC

P564 (entire underlined)

FIG. 10 (SEQ ID NO:6)

P215 (entire underlined)

NT7 bidirectional promoter, partially.
(larger standard font)

AAGCAAGAGACGGAACAAGATGGACGACGCGTCTGCAACAGACCGGCTCGCGCCGAACGTGCCTCCTGCTTTTCAACGATCCTG
CGAGGTCAACCAGGATTTGCTCGCCCGGACGATTTCATCCCCTTATCAACGAGCCCTTGAGGCTCCAGGCGTGCTT
CCACACCCCAGTTGGTAACAGAGACATTGGGCATCTGCCTATCTGTCTTAGTGCCGAAAGCCTCAACGACCTCC
CATGGGGTCTGCTCAACGCCCTCAACCTTGCAGTAAGGATCCCCGAGGGCAAGACCCGCAAAGCCTTCTGTCGTCGG
ACAAAGCGGAGCGAGGGAACAGGCTCAGCTCAACCCTCTTGAGAGCCCATAAGTGCCCCCTGATCTATCTTCAACA
GTCTTTCCCTGTCACAAGAAAACCCAGCTAGTTGACCAAGTTGCTAGAGCTGATACCTTGTACTTCGCTCTTTGTG
TGCTTTACCTGATTGGACATGGACAGACCTCCCCTTGCTCTCTTTCCTTCTAGGAGCCTGGGCTCTCGCTCTGTTCTT
TCGAGAGACCTTTCCCTTGAGTTGCGTATCCAGCGATCAAGTATGAAGAGTGCTTTCAAACCTAGATACGTTCTGC
CCAGTTCTCTCTTGCCCTTTTCCACACGTCCTCCACATCTTCACACGACTCGCACCATACCCGACGAAACCCTCAAA
ACATCGCAACACTTACATCCCGCTCGTGTCCCACCCCCGATGCCATATCCTCTACAGCAGCACCACCACCACC
ACTTCTTAAGT

P113 (entire underlined)    ATG = start codon *sh ble* gene

ATGGCCAAGTTGACCAGTGCCGTTCCGGTTCCGGCTGCTCACCGCGCGCCGGAGCGGTCGAGTTCTGGACCGACCGGCTCGGGTTCTC
CCGGGACTTCGTGGAGGACGACTTCGCCGGTGTGGCGCCTGTTCATCAGCGCGGTCCAGGACCCAGGTGTGCCGG
ACAACACCCTGGCCTGGGTGTGGGCGCGGAGATCGGCCGAGCAGAGCTGTACGCGGAGGTGGTGTCCACGAACTTCCGGGACGCC
TCCGGCCGGCCATGACCGAGATCGGGGAGGACGCGCGAGCAGCGGCGAGTTGCGCCCTGGCGCGACCCGGAGTTGCCACTTCGT
GGCCGAGGAGGAGGACTAA

P266 (entire underlined)    UTR of NT7 Transformation construct, partially (larger font in italics)

*GCTTCTCTGTGGAAGAGCCAGTGGTAGTAGCAGCAGCAGCAGTAGCAGCAGCCGCAGCAGCACTCAGTGTTGGCGCGAGAG
ATTGTCCATCCCTTCTTAACCTACCGGAAGAGAAATAAGGCCTTTCTCCCCGTAGCCTTCTTCGTTTGTTTGTGCTG
ATTGCTTGATATGAGAGTGTTGAATTCCTGCATCATGTTTTCTCTGTAGTCCTTTCCTACCCCGTCATTTTCTT
TTCTCCCTGGTTCTTCTTTTGTCACCCTTTATTTACATAAAATTTCTTTGTTTATAGTGAGAGGAAGGTAGAGAG
GGGAAAAACAAGAACAACGAACGCCAAGCGTGTGAA*

FIG. 11 (SEQ ID NO:7)

P215 (entire underlined)

AAGCAAGACGGAACAAGATGGCACGGCTCTGCAACAGACCGGCTCGCGCCCGAACGTGCCTCCTGCTTTCAACGATCTGCGAGGTCAACCAGGA
TTTGCTCGCCGGGACGATTTCATCCCCTTATCAACGAGCCCTTGAGGCTCCAGGCGTCCAGCGTGCTTCCACACCCCAGTTGGTAACAGGACATTGGGCAT
CTTGCCTATCTTGTCTTAGTGCCGAAAGCCTCAACGACCTCAACGCCTGCTCAACGCCTCTTGCAGTTTGCAGTAAGGATCCCCGAGGCAAGA
CCCGCAAAGCCTTCGTCGTCGGACAAGAAAAACCAGCTAGTTGACCAAGTTGCTAGAGCTGATACCTTGTACTTCGCTCTTTGTGCTTACCTGATTG
AACAGTCTTTCCCGTCACAAGAGAAAAACCAGCTAGTTGACCAAGTTGCTAGAGCTGATACCTTGTACTTCGCTCTTTGTGCTTACCTGATTG
GACATGGACAGACCTCCCCTTGCTCTTCCTTCACAAGAGAGCCTGGGCCTTCTCGCCCAGTTCTCTTGCCCCTTTTCCACACGTGCTCCACATCTTCACACGACTCGCAC
GATCAAGTATGAAGAGTGCTTTCAAACCTAGATACGTTCTGCCCAGTTCTCTTGCCCCTTTTCCACACGTGCTCCACATCTTCACACGACTCGCAC
CATACCCGACGAAACCCTCAAAAACATCGCAACACTTACATCCCGCTCGTGTCCCACCCCGATGCCATATCCTCTACAGCAGCAGCACCACCAC
CACCACTTCTTAAGT
ATGGCCAAGTTGACCAGTGCCGTTCCGGTGCTCACCGCGCGCGACGTCGCCGGAGCGGTCGAGTTCTGGACCGACCGGCTCGGGTTCTCCCGGGA
CTTCGTGGAGGACGACTTCCGCGGTGTGGTCCGGTGACGACGTGACCCTGTTCATCAGCGCGGTGACCGGCGTGCCGGACAACACCCTGG
CCTGGGTGTGGTGGCCGGCCTGGACGAGCTGTACGCCGAGGGCGGGAGTTCGCCCTGCGACCCGGGCGGCCAACTTCGTGTCGACTTCGTCCATGACC
GAGATCGGCGAGCAGCCGTGGGGGCGAGCCAGTAGTGGTAGCAGCAGTAGCAGCCGCAGCACTCAGTGCTGATTGTCATCCCTTCTTAACCTAC
TGTGGAAGAGCCAGTGGTAGTAGCAGGGAGTAGCAGCCGCAGCACTCAGTGCTGATTGTCATGAGAGGTGTTGAATTCTGCATCATGTTTTC
CGGAAGAGAAATAAGGCCTTTCCTACCCCCGTCATTTCTTTCTCCCGTCATTTGTGTCACCCTTATTTACATAAAAATTTCTTTGTTTATAGTGAG
TCTGTAGTCCTTTCCTACCCCCGTCATTTCTTTCTCCCGTCATTTGTGTCACCCTTATTTACATAAAAATTTCTTTGTTTATAGTGAG
AGGAAGGTAGAGAGGGAAAACAAGAACAACGAACAACGAACGTGTGAA

TGTTCTCACCATGTCTCCTGCCAT
GGCCCCACGTCTCTTGCGTCGGGCGTGTGCGTTTTGAGAATGGGTGACAGGGAAGCGAACACAGGCTAAGGGAGACGCATGCG
TCGGCGGGTCTCGACACTCCACGCCCTTGTCGGCAGAAAGGCGACGCACGAGCGCAAAAGCACTAGAAGGCCTTTCTTGGGC
ATCTTTTCTCTGTACGGCCCCTTGCTTTGGTCAACGTCGACACCTCTCCCAACATGCACGCAGAGTGATCTCCGGTGTG
GGAGGCTGCGCCGTTGCTTTGGTCAACGTCGACACCTCTCCCAACATGCACGCAGAGTGATCTTCGGTGTG
ATGTTGCGTGAACGGCCTTTGTGCGACCATGCTGCCACCATTGCCTACACGACCATCGCAAGCTTCGCAAGCCTTAGCTTGCTTCGCG
TCAGGCTTCGATACTCTGCGACCATGCTGCCACCATTGCCTACACGACCATCAACACATCAGCACACCGTACACCCGGGTCGGCAGACGTGGTGAAAGCGCCCATGCTGTAACGCGTACACCGTGCCTCTCCGGGTCGGCAGACGTGGTGAAAGCGCCCATGCTGTAACGCGTACACCGTGCCTCTCCTTACTCTATTCAAGCGTGCTGC
ACACGCGCACAAACACACACACACCCGCCACCAGTAGAACCAGCAACATCAGCAACACACACACACCCGCCACCAGTAGAACCAGCAACATCAGCAACACACACACCCGCCACCAGTAGAACCAGCAACATCAGCAACACACACCCGCCACCAGTAGAACCAGCAACATCAGCAACACACACCCGCCACCAGTAGAACCAGCAACATCAGCAACACACACCCGCCACCAGTAGAACCAGCAACATCAGCAACACACACCCGCCACCAGTAGAACCAGCAACATCAGCAACACACACCCGCCACCAGTAGAACCAGCAACATCAGCAACACACCGTGCCTCTCCTTACTCTATTCAAGCGTGCTGC
GTGCCTTTGACTTCATTCCTGCGATCCATCCCCTTCTGACTCTACTCAGTC
TTCCCCACATCCCCTACTACTCCCCTCTTCTCATCTCTACAGTC

ACACCTTCCTCCTCTTCACTTAACC ◄─── P564 rev fusion         ACP Promoter (larger standard font)

FIG. 12 (SEQ ID NO:8)

P525 TGTTCTCACCATGTCTCCTGCCAT (SEQ ID NO:9)

P526 ACGGCACTGGTCAACTTGGCCAT ggttaagtgaagagaggaggaaggtgtgactgt (SEQ ID NO:10)

P563 GAACAACGAACGCAAGGCGTGTGAA TGTTCTCACCATGTCTCCTGCCAT (SEQ ID NO:11)

P564 ggttaagtgaagagaggaggaaggtgtgactgt (SEQ ID NO:12)

P113 ATG GCC AAG TTG ACC AGT GCC GT (SEQ ID NO:13)

P215 AAGCAAGACGGAACAAGATGGCAC (SEQ ID NO:14)

P266 TTCACACGCTTGCGTTCGTTGTTC (SEQ ID NO:15)

FIG. 13 (SEQ ID NO:9-15)

```
GGCCCCACGTCTTGCGTCGGGGTGTGGCGTTTGAGAATGGGTGACAGGGAAGCGAACACAGGCTAAGGGAGACGCAT
GCGTCGGCGGGTCTCGACACTCCACGCCTTGTGCGGCAGACGCAGCCAAAAGCACTAGAAGGCCTTTCT
TGGGCATCTTTTCTCTGTACGGCCCCTTATCAGCCTGTCTATTGTGTGCGCCCTTGCGTGCGCCCTTGACATCGATTAC
TCCGGGAGGCTGCGCGGCCGTTGGTTCAACGTGACACGACAACATGCACGGCAGAGTGATCTTCGG
GTGTGATGTTGCGTGAACGGCCTTTGTGCGACCACTCTTCACCGGCCATCCGCAAGCTTATAGACC
TTATATCAGGCTTCGATACTCTGCGACCATGCTTCGCACCATTGCTACACGGGCTCGGCAGAGAGTGGTGAAGCCGAGCTTAGCTTGC
TTCGGTCCTATGATGATTCCACACACCATTGCCTACACGACACGATACACCGTACACGCCCATGCTACACCTGCTACAC
ACGGCGACACGCCACAAACACACATACATCAACACACAATACAGCAATCCGTGCCTCTCTTACTCTATTCAAGC
GTGCTGCGTGGCCTTTGACTTCATTCCTTGTCCACCGGCCACCAGTAGAACCAGCACCAGCACCAGCACCAGCACCAGTCCACCCTCATCTCAC
TCCTCTTTCCCCCACATCCCCTACTACTCCATCCTTCTCATCT
```

FIG. 14 (SEQ ID NO:16)

ACP PROMOTER

CROSS-REFERENCE TO RELATED APPLICATIONS

The present application claims the benefit and priority of U.S. Provisional Patent Application Ser. No. 61/640,084 filed on Apr. 30, 2012, titled "ACP Promoter," which is hereby incorporated by reference.

The present application is related to U.S. Non-Provisional patent application Ser. No. 12/706,683 filed on Feb. 16, 2010, and issued as U.S. Pat. No. 8,314,228 on Nov. 20, 2012, titled "Bidirectional Promoters in *Nannochloropsis*," which is hereby incorporated by reference.

The present application is related to U.S. Non-Provisional patent application Ser. No. 12/480,635 filed on Jun. 8, 2009, and issued as U.S. Pat. No. 8,318,482 on Nov. 27, 2012, titled "VCP-Based Vectors for Algal Cell Transformation," which is hereby incorporated by reference.

REFERENCE TO SEQUENCE LISTINGS

The present application is filed with sequence listing(s) attached hereto and incorporated by reference.

BACKGROUND OF THE INVENTION

Field of the Invention

This invention relates to molecular biology, and more specifically, to algal promoters.

SUMMARY OF THE INVENTION

Isolated nucleotide sequences encoding a promoter of the Acyl Carrier Protein ("ACP").

BRIEF DESCRIPTION OF THE DRAWINGS

FIG. 5 shows the nucleotide sequence of an ACP gene in the *Nannochloropsis* genome (SEQ ID NO:1).

FIG. 6 shows the nucleotide sequence an ACP gene transcript as predicted by transcriptome analysis (SEQ ID NO:2).

FIG. 7 shows the nucleotide sequence of the ACP promoter when amplified by the P525 and P526 primers (SEQ ID NO:3).

FIG. 8 shows the nucleotide sequence of the sh ble gene—3' untranslated region as amplified by the P113 and P266 primers. The sh ble gene—3' untranslated region represents part of the NT7 transformation construct as illustrated in FIG. 1 (SEQ ID NO:4).

FIG. 9 shows the nucleotide sequence of the ACP promoter—sh ble gene—3' untranslated region transformation construct as illustrated in FIG. 2 (SEQ ID NO:5).

FIG. 10 shows the nucleotide sequence of the ACP promoter when amplified by the P563 and P564 primers (SEQ ID NO:6).

FIG. 11 shows the nucleotide sequence of the NT7 transformation construct of FIG. 1 when amplified by the P215 and P266 primers (SEQ ID NO:7).

FIG. 12 shows the nucleotide sequence of the ACP activator construct as illustrated in FIG. 3 that was generated by fusing SEQ ID NO:6 and SEQ ID NO:7 with the primers P564 and P215 (SEQ ID NO:8).

FIG. 13 shows the nucleotide sequences of primers:
P525 (SEQ ID NO:9);
P526 (SEQ ID NO:10);
P563 (SEQ ID NO:11);
P564 (SEQ ID NO:12);
P113 (SEQ ID NO:13);
P215 (SEQ ID NO:14); and
P266 (SEQ ID NO:15).

FIG. 14 shows the nucleotide sequence of the ACP promoter (SEQ ID NO:16).

DETAILED DESCRIPTION OF THE INVENTION

Identified herein is a new strong promoter for the expression of genes in *Nannochloropsis*.

The Acyl Carrier Protein ("ACP") is a protein used in various metabolic processes, such as in fatty acid biosynthesis. Whole transcriptome analysis of log phase growth cultures and cultures growing under Nitrogen starvation revealed a very high expression of this small protein. High transcript representation under either of these conditions prompted the inventors to use the ACP promoter within selection markers for the transformation of *Nannochloropsis*.

Figure 1:
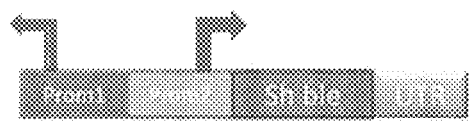
FIG. 1 illustrates an exemplary NT7 transformation construct.

FIG. 1 illustrates an exemplary NT7 transformation construct as illustrated and described in U.S. Non-Provisional patent application Ser. No. 12/706,683 filed on Feb. 16, 2010, and issued as U.S. Pat. No. 8,314,228 on Nov. 20, 2012, titled "Bidirectional Promoters in *Nannochloropsis*," which is hereby incorporated by reference. FIG. 1 includes a VCP bidirectional promoter comprising "Prom1", "Prom2", a sh ble gene and the UTR of a different VCP gene ('UTR'). The sh ble gene is from *Streptoalloteichus hindustanus* and confers resistance to the antibiotic Zeocin. As shown in FIG. 1, replacement of the bidirectional promoter with the ACP promoter yields the construct depicted in FIG. 2, where sh ble gene expression is driven by the ACP promoter.

Figure 2:
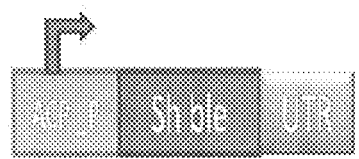
FIG. 2 illustrates an ACP promoter—sh ble gene—3' untranslated region transformation construct.

FIG. 2 illustrates an ACP promoter—sh ble gene—3' untranslated region transformation construct. The ACP promoter drives expression of the sh ble gene (that is attached to a VCP1 untranslated region) and proved to be suitable as a highly active promoter in high efficiency transformation constructs.

Figure 3:
FIG. 3 illustrates a VCP promoter—sh ble gene—3' untranslated region—ACP promoter transformation construct ("ACP activator construct").

FIG. 3 illustrates a VCP promoter—sh ble gene—3' untranslated region—ACP promoter transformation construct ("ACP activator construct"). The ACP activator construct comprises the second half of the bidirectional promoter ("Prom2", as in FIG. 1), the sh ble gene, the UTR of a different VCP gene ('UTR') and the ACP promoter ("ACP_P"). The inventors attached the ACP promoter to existing constructs, such as the NT7 transformation construct. The NT7 construct had been truncated (first half of bidirectional promoter removed, while the other half is still present to drive expression of the sh ble gene. The ACP promoter had been added after the NT7 UTR region to the right). When fused to such a construct at the 3' end as shown in FIG. 3, the ACP promoter acted as an activator for downstream genes when the entire construct inserted randomly into the *Nannochloropsis* genome. The inventors constructed an insertional activator library (>50.000 cultivars) in which genes were either randomly interrupted by insertion of the entire construct (FIG. 4C) or genes downstream of the transformation construct were activated (i.e. transcription of downstream genes enhanced by the strong ACP promoter FIG. 4D). FIG. 3 shows the actual ACP-activator construct, which is based on a truncated version of the NT7 construct from FIG. 1 (i.e., one half of the bidirectional promoter was omitted and the ACP promoter was added after the UTR region).

FIGS. 4A-4E illustrate the activator construct (VCP promoter—sh ble gene—3' untranslated region—ACP promoter transformation construct) and transformation results when the construct is used under various exemplary situations.

Figure 4:
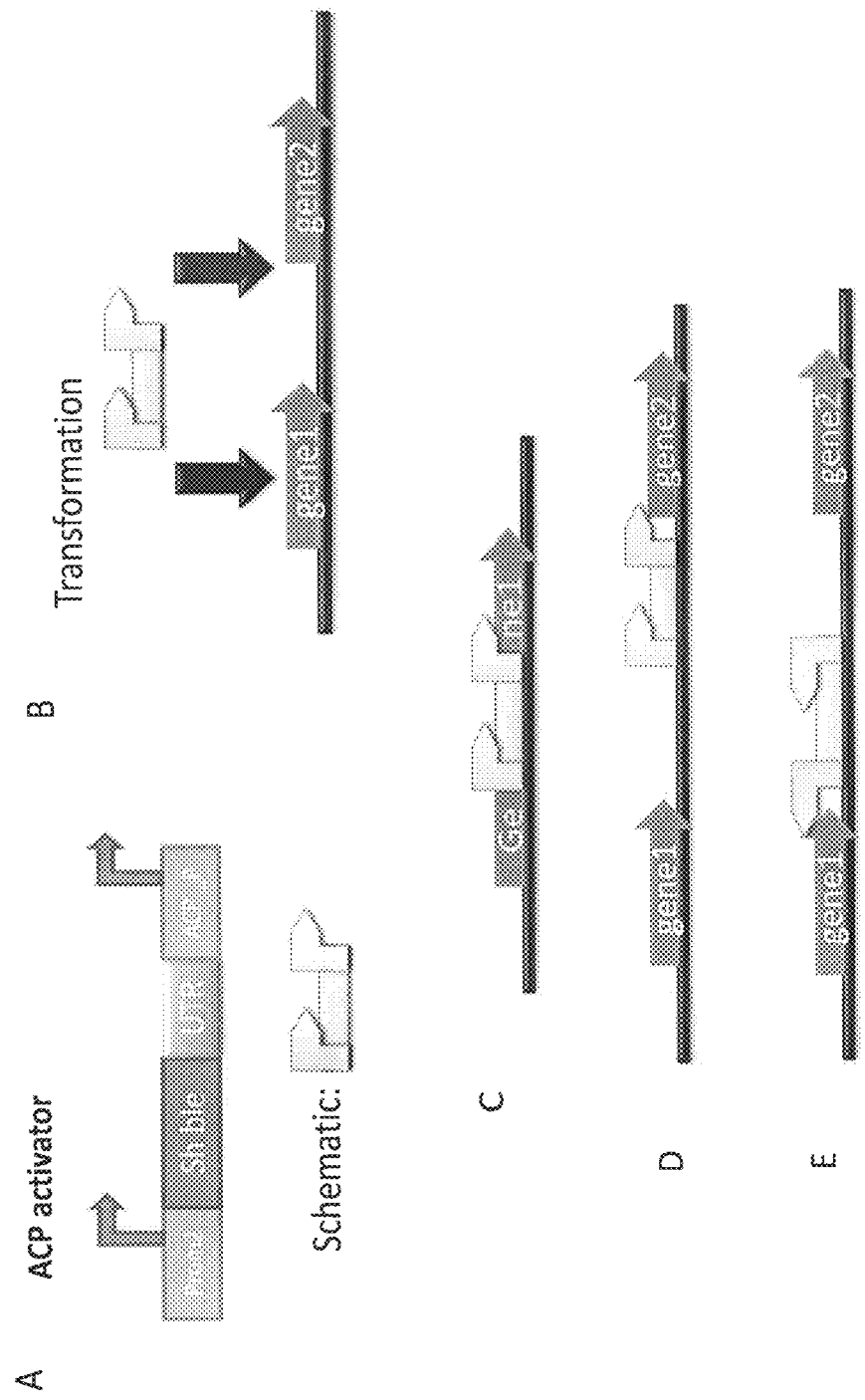
FIGS. 4A-4E illustrates the VCP promoter—sh ble gene—3' untranslated region—ACP promoter transformation construct ("ACP activator construct") and transformation results when the construct is used under various exemplary situations.

An activator construct (FIG. 4A) may randomly insert into the *Nannochloropsis* genome (e.g. FIG. 4B) and may either interrupt a gene and thus render it dysfunctional (FIG. 4C) or insert in front of a gene (FIG. 4D) and thus enhance transcription of the gene. If insertion occurs with the ACP promoter pointing in a direction opposite the direction that a gene is expressed, transcription of such a gene could be down regulated (FIG. 4E).

FIG. 5 shows the nucleotide sequence of the ACP gene in the *Nannochloropsis* genome (SEQ ID NO:1). FIG. 5 shows primer P525, primer P526, the start codon of the ACP gene, Intron I, Intron II, and the stop codon of the ACP gene.

FIG. 6 shows the nucleotide sequence of an ACP gene transcript as predicted by transcriptome analysis (SEQ ID NO:2).

FIG. 7 shows the nucleotide sequence of the ACP promoter when amplified by the P525 and P526 primers (SEQ ID NO:3). FIG. 7 shows a PCR product obtained with primer P525 and primer P526. P525×P526 Polymerase Chain Reaction ("PCR") on genomic DNA yielded a DNA fragment suitable for fusing to the sh ble gene with the respective UTR as found in NT7, as shown in SEQ ID NO:4 (as amplified by P113×P266). SEQ ID NO:3 and SEQ ID NO:4 were fused via PCR using primers P525×P266 to yield an ACP promoter—sh ble gene—3' untranslated region transformation construct as illustrated in FIG. 2 and equivalent to SEQ ID NO:5 of FIG. 9.

FIG. 8 shows the nucleotide sequence of the sh ble gene—3' untranslated region as amplified by the P113 and P266 primers (SEQ ID NO:4). The sh ble gene—3' untranslated region represents part of the NT7 transformation construct of FIG. 1. FIG. 8 shows the start codon of the sh ble gene, primer P113, UTR of NT7 transformation construct (partially), and primer P266.

FIG. 9 shows the nucleotide sequence of the ACP promoter—sh ble gene—3' untranslated region transformation construct as illustrated in FIG. 2 (SEQ ID NO:5). FIG. 9 shows primer P525, the ACP promoter, primer P113, the start codon of the sh ble gene, UTR of NT7 transformation construct (partially), and primer P266.

FIG. 10 shows the nucleotide sequence of the ACP promoter when amplified by the P563 and P564 primers (SEQ ID NO:6). P563×P564 PCR on genomic DNA yielded the same ACP promoter sequence of SEQ ID NO:3, but suitable for fusion on a partial NT7 transformation construct as evidenced by SEQ ID NO:7 as shown in FIG. 11.

FIG. 11 shows the nucleotide sequence of the NT7 transformation construct of FIG. 1 when amplified by the P215 and P266 primers (SEQ ID NO:7). As shown in FIG. 11, the second half of the bidirectional VCP promoter sequence is driving the expression of the sh ble gene.

FIG. 12 shows the nucleotide sequence of the ACP activator construct as illustrated in FIG. 3 that was generated by fusing SEQ ID NO:6 and SEQ ID NO:7 with the primers P215 and P564 (SEQ ID NO:8). FIG. 12 shows the ACP activator construct illustrated in FIG. 3.

FIG. 13 shows the nucleotide sequences of primers:
P525 (SEQ ID NO:9);
P526 (SEQ ID NO:10);
P563 (SEQ ID NO:11);
P564 (SEQ ID NO:12);
P113 (SEQ ID NO:13);
P215 (SEQ ID NO:14); and
P266 (SEQ ID NO:15).

FIG. 14 shows the nucleotide sequence of the ACP promoter (SEQ ID NO:16).

A transformation construct or vector may comprise any number of promoters, genes, and/or other nucleic acid polymers (naturally occurring or synthetic) and/or their analogs, or other compounds that do not interfere with the ability of the transformation construct to enter the algal cell or the algal genome, or to function. In some embodiments, additional nucleotides may appear in the transformation construct to facilitate or direct the insertion of the construct (or any part thereof) into a desired location in the genome.

While various embodiments have been described above, it should be understood that they have been presented by way of example only, and not limitation. Thus, the breadth and scope of a preferred embodiment should not be limited by any of the above-described exemplary embodiments.

---

What is claimed is:

1. A transformation vector comprising heterologous nucleic acid sequences and the nucleotide sequence comprising SEQ ID NO: 16.

* * * * *

SEQUENCE LISTING

```
<160> NUMBER OF SEQ ID NOS: 16

<210> SEQ ID NO 1
<211> LENGTH: 3001
<212> TYPE: DNA
<213> ORGANISM: Nannochloropsis

<400> SEQUENCE: 1
accgagtgaa gcaacgccag agctatggac aaggaatcca aggagataac tgtatttcac      60
gcaccttctt tgacctcctt ctctcaaccc ccaacatttc gcatgcccat tcggtcataa     120
tcctgtgggc tcgctgctct cgcctttgct gcctccgcgt cgacgcatcc agtccttccg     180
tccctgctct attcacacgt ctacaatttt ccatatgcat gagttgcaat ctttgccctc     240
tctgttctca ccatgtctcc tgccatggcc ccacgtcttg cgtcggggct gtggcgtttt     300
```

-continued

| | |
|---|---|
| gagaatgggt gacagggaag cgaacacagg ctaagggaga cgcatgcgtc ggcgggtctc | 360 |
| gacactccac gccttgtcgg cagaaaggcg acgcacgagc caaaaagcac tagaaggcct | 420 |
| tttcttgggc atcttttctc tgtacggccc cttatcagcc tgtcttattg tgctggtgtt | 480 |
| gcttgcgtgc gcccttgaca tcgattactc cgggaggctg cgcggccgtt gctttggtca | 540 |
| acgtcgacac gacacctctc cccaacatgc acggcagagt gatcttcggg tgtgatgttg | 600 |
| cgtgaacggc ctttgtgcca cttctttcac cggcccaacc ataccgcat ccactcgcaa | 660 |
| gcttatagac cttatatcag gcttcgatac tctgcgacca tgcttcgcac cgggctcggc | 720 |
| agagacgtgg tgaaagccga gccttagctt gcttcgcgtc ctatgatgat tccaccacca | 780 |
| ttgcctacac gacacgatac acccgtacac gcccatgcta caccctgcct acacacgcgc | 840 |
| acacgcgcac aaacacacac atacatcaac acacacaata cagcaatccg tgcctctctc | 900 |
| ttactctatt caagcgtgct gcgtggcctt tgacttcatt cctcttgtcc acccgccggc | 960 |
| caccagtaga accagcacca cgtccaccct catctcactc ctctttcccc cacatcccct | 1020 |
| actactccat ccttctcatc tacagtcaca ccttcctcct cttcacttaa ccatgcgtgt | 1080 |
| ccttgctttc ttcgccctcc tggccgcacc cgccctggcc ttcgtgcccc gtatgcccgc | 1140 |
| ccccgtgcgt gcccgcgcca gtctcaccct ccgattctct ggagagtaca gcgagaaggt | 1200 |
| aagccacctc tctttccttc atgtcctatc ttgcgccctc cttccccatg cttcttcccc | 1260 |
| gatattttgt ggtcagttct tggtgtgtca ccttggggtg ggcgggtgaa ccgcagcgat | 1320 |
| ttctctttca gggatgtggg ggctggatgc ccgtcttggc tacctttccc ttccctccct | 1380 |
| ggtcccgtcc cttctcctcc cttttcactt ctctctcttt ttttcttcc tctcccctc | 1440 |
| ctcgaacttc ccctggccga aagtgatcca tgtcccactt tcacttaccc gccctccctc | 1500 |
| cctccctccc cctctccctc caggtgcgcg ccatcgtgtt ggagaacatg ggcgatgatg | 1560 |
| ccaaggtgca ggactacctg aaggccaacg gtgatgataa ggccgagttc gccgccatgg | 1620 |
| gctttgattc tttggacttg gtggagttct ccatggccat ccagaaggta cgggaacctg | 1680 |
| ccttccttct ctccctccct cccaacctac ttcccttcca tcacggcgcc gagctctctg | 1740 |
| tctccgatct catgggtata tcgttgtgtc tgcctcgtcg agcccgtagt ttagacatcg | 1800 |
| atatcattct catgcactcc atcaaatgaa aattaatatt aatttccac tcacatactc | 1860 |
| tcccctccct tccttcctct cttctcagga gttcgacctc ccggacctga acgaggagga | 1920 |
| cttcgccaac ctcaagacga tcaaggacgt ggtcactatg gtggaggcca caagaagta | 1980 |
| aacacacaac ggcagcgaca gcagcagcac cagcagcatg cacgagggga ggaggaagat | 2040 |
| gactcggttg ttggttggtg tgttgacgta ttgtgatatg tgtgcattct caccctaatt | 2100 |
| ggtcttcaca tctcctctcg tctcccttc ctggaaggg atggcgggaa ggaaagaggg | 2160 |
| agggagtgct tgtgtgtgct atgttgtgtt tcgtgtggca tgactggagg tgggcgatta | 2220 |
| acagcaagag gagaaattgg gctgaatgaa cgcttaagtc gtgtctgtgt ttgtgacgat | 2280 |
| gagtggggag gacgtagcct catcccccct ttcttcccgg tcggtctttt tcggccttt | 2340 |
| cctccttccc ctccaagggt ggaaggagga ggatggacag ggcgagagac aagagaagga | 2400 |
| tggggctaga gaatccacac acaactagag atagaagtac tttatccttg ttctccttct | 2460 |
| tgttattgac gtgttgattt ttggtcctct tcttgcgcgc gatctttctc tcgttcgtcg | 2520 |
| atctttcgtc ttttttttctt ttgtcaactc tctctctctt caccgacgcc tcttcgaaga | 2580 |
| atctatttcc tctctacttc tgccctctcg tgtcttaaat ttaatcctcg cggttttcgt | 2640 |
| cttctctccc tccaccacca atcccttctc cttttctcgtc cccttccaca tccccccac | 2700 |

| | |
|---|---|
| cccctcctcc taaacctgtt tcactgtggc cctccgcgat gaagatgccc gattggtgcg | 2760 |
| tgccctgtca tatgtacgca tatatctata attgtttata catatttaaa ttctttcctt | 2820 |
| cccttctcaa gccctgtgg ctttgtctct attcgtctcc ttctgcccgc ctccgcgttc | 2880 |
| cttccccccc cctccctcac ggcctccctc ctcacctcgg gtgcctgcgt ctcctgccct | 2940 |
| cgatcgaacc gcgcagtgaa ttcagttgtc acacgaggat gttcgcctgg ggccgtgggg | 3000 |
| t | 3001 |

<210> SEQ ID NO 2
<211> LENGTH: 623
<212> TYPE: DNA
<213> ORGANISM: Nannochloropsis

<400> SEQUENCE: 2

| | |
|---|---|
| acagtcacac cttcctcctc ttcacttaac catgcgtgtc cttgctttct tcgccctcct | 60 |
| ggccgcaccc gccctggcct tcgtgccccg tatgcccgcc ccgtgcgtg cccgcgccag | 120 |
| tctcacccct cgattctctg gagagtacag cgagaaggtg cgcgccatcg tgttggagaa | 180 |
| catgggcgat gatgccaagg tgcaggacta cctgaaggcc aacggtgatg ataaggccga | 240 |
| gttcgccgcc atgggctttg attctttgga cttggtggag ttctccatgg ccatccagaa | 300 |
| ggagttcgac ctcccggacc tgaacgagga ggacttcgcc aacctcaaga cgatcaagga | 360 |
| cgtggtcact atggtggagg ccaacaagaa gtaaacacac aacggcagcg acagcagcag | 420 |
| caccagcagc atgcacgagg ggaggaggaa gatgactcgg ttgttggttg gtgtgttgac | 480 |
| gtattgtgat atgtgtgcat ctcaccccta attggtcttc acatctcctc tcgtctccct | 540 |
| ttcctgggaa gggatggcgg gaaggaaaga gggagggagt gcttgtgtgt gctatgttgt | 600 |
| gtttcgtgtg gcatgactgg agg | 623 |

<210> SEQ ID NO 3
<211> LENGTH: 853
<212> TYPE: DNA
<213> ORGANISM: Nannochloropsis

<400> SEQUENCE: 3

| | |
|---|---|
| tgttctcacc atgtctcctg ccatggcccc acgtcttgcg tcggggctgt ggcgttttga | 60 |
| gaatgggtga cagggaagcg aacacaggct aagggagacg catgcgtcgg cgggtctcga | 120 |
| cactccacgc cttgtcggca gaaaggcgac gcacgagcca aaaagcacta gaaggccttt | 180 |
| tcttgggcat ctttttctctg tacgcccct atcagcctg tcttattgtg ctggtgttgc | 240 |
| ttgcgtgcgc ccttgacatc gattactccg ggaggctgcg cggccgttgc tttggtcaac | 300 |
| gtcgacacga cacctctccc caacatgcac ggcagagtga tcttcgggtg tgatgttgcg | 360 |
| tgaacggcct ttgtgccact tctttcaccg gcccaaccat acccgcatcc actcgcaagc | 420 |
| ttatagacct tatatcaggc ttcgatactc tgcgaccatg cttcgcaccg ggctcggcag | 480 |
| agacgtggtg aaagccgagc cttagcttgc ttcgcgtcct atgatgattc caccaccatt | 540 |
| gcctacacga cacgatacac ccgtacacgc ccatgctaca ccctgcctac acgcgcac | 600 |
| acgcgcacaa acacacacat acatcaacac acacaataca gcaatccgtg cctctctctt | 660 |
| actctattca agcgtgctgc gtggcctttg acttcattcc tcttgtccac ccgccggcca | 720 |
| ccagtagaac cagcaccacg tccaccctca tctcactcct ctttccccca catcccctac | 780 |
| tactccatcc ttctcatcta cagtcacacc ttcctcctct tcacttaacc atggccaagt | 840 |
| tgaccagtgc cgt | 853 |

<210> SEQ ID NO 4
<211> LENGTH: 713
<212> TYPE: DNA
<213> ORGANISM: Nannochloropsis

<400> SEQUENCE: 4

```
atggccaagt tgaccagtgc cgttccggtg ctcaccgcgc gcgacgtcgc cggagcggtc      60
gagttctgga ccgaccggct cgggttctcc cgggacttcg tggaggacga cttcgccggt     120
gtggtccggg acgacgtgac cctgttcatc agcgcggtcc aggaccaggt ggtgccggac     180
aacaccctgg cctgggtgtg ggtgcgcggc ctggacgagc tgtacgccga gtggtcggag     240
gtcgtgtcca cgaacttccg ggacgcctcc gggccggcca tgaccgagat cggcgagcag     300
ccgtgggggc gggagttcgc cctgcgcgac ccggccggca actgcgtgca cttcgtggcc     360
gaggagcagg actaagcttc tgtggaagag ccagtggtag tagcagtagc agcagcagta     420
gcagccgcag cactcagtgt tggcgcgaga gattgtccat cccttcttaa cctaccggaa     480
gagaaataag gcctttctcc cgtagctgtc ttcgtttgtt tgtgctgatt gcttgatatg     540
agagtgttga attcctgcat catgtttttc tctgtagtcc tttcctaccc ccgtcatttt     600
cttttctccc tggttcttct tttgtcaccc ttattttaca taaaattttc tttgtttata     660
gtgagaggaa ggtagagagg ggaaaacaag aacaacgaac gcaagcgtgt gaa            713
```

<210> SEQ ID NO 5
<211> LENGTH: 1543
<212> TYPE: DNA
<213> ORGANISM: Nannochloropsis

<400> SEQUENCE: 5

```
tgttctcacc atgtctcctg ccatggcccc acgtcttgcg tcggggctgt ggcgttttga      60
gaatgggtga cagggaagcg aacacaggct aaggagacg catgcgtcgg cgggtctcga     120
cactccacgc cttgtcggca gaaaggcgac gcacgagcca aaaagcacta gaaggccttt     180
tcttgggcat cttttctctg tacggcccct tatcagcctg tcttattgtg ctggtgttgc     240
ttgcgtgcgc ccttgacatc gattactccg ggaggctgcg cggccgttgc tttggtcaac     300
gtcgacacga caccctctcc caacatgcac ggcagagtga tcttcgggtg tgatgttgcg     360
tgaacggcct ttgtgccact tctttcaccg gcccaaccat acccgcatcc actcgcaagc     420
ttatagacct tatatcaggc ttcgatactc tgcgaccatg cttcgcaccg ggctcggcag     480
agacgtggtg aaagccgagc cttagcttgc ttcgcgtcct atgatgattc caccaccatt     540
gcctacacga cacgatacac ccgtacacgc ccatgctaca ccctgcctac acacgcgcac     600
acgcgcacaa acacacacat acatcaacac acacaataca gcaatccgtg cctctctctt     660
actctattca agcgtgctgc gtggcctttg acttcattcc tcttgtccac ccgccggcca     720
ccagtagaac cagcaccacg tccaccctca tctcactcct cttctcccca catccctac     780
tactccatcc ttctcatcta cagtcacacc ttcctcctct tcacttaacc atggccaagt     840
tgaccagtgc cgttccggtg ctcaccgcgc gcgacgtcgc cggagcggtc gagttctgga     900
ccgaccggct cgggttctcc cgggacttcg tggaggacga cttcgccggt gtggtccggg     960
acgacgtgac cctgttcatc agcgcggtcc aggaccaggt ggtgccggac aacaccctgg    1020
cctgggtgtg ggtgcgcggc ctggacgagc tgtacgccga gtggtcggag gtcgtgtcca    1080
cgaacttccg ggacgcctcc gggccggcca tgaccgagat cggcgagcag ccgtgggggc    1140
gggagttcgc cctgcgcgac ccggccggca actgcgtgca cttcgtggcc gaggagcagg    1200
```

```
actaagcttc tgtggaagag ccagtggtag tagcagtagc agcagcagta gcagccgcag   1260
cactcagtgt tggcgcgaga gattgtccat cccttcttaa cctaccggaa agaaataag    1320 gcctttctcc cgtagctgtc ttcgtttgtt tgtgctgatt gcttgatatg agagtgttga   1380
attcctgcat catgttttc tctgtagtcc tttcctaccc ccgtcatttt ctttctccc     1440 tggttcttct tttgtcaccc ttattttaca taaaattttc tttgtttata gtgagaggaa   1500
ggtagagagg ggaaaacaag aacaacgaac gcaagcgtgt gaa                     1543

<210> SEQ ID NO 6
<211> LENGTH: 854
<212> TYPE: DNA
<213> ORGANISM: Nannochloropsis

<400> SEQUENCE: 6
gaacaacgaa cgcaagcgtg tgaatgttct caccatgtct cctgccatgg ccccacgtct    60
tgcgtcgggg ctgtggcgtt ttgagaatgg gtgacaggga agcgaacaca ggctaaggga   120
gacgcatgcg tcggcgggtc tcgacactcc acgccttgtc ggcagaaagg cgacgcacga   180
gccaaaaagc actagaaggc ttttcttgg gcatcttttc tctgtacggc cccttatcag    240
cctgtcttat tgtgctggtg ttgcttgcgt gcgcccttga catcgattac tccgggaggc   300
tgcgcggccg ttgctttggt caacgtcgac acgacacctc tccccaacat gcacggcaga   360
gtgatcttcg ggtgtgatgt tgcgtgaacg gcctttgtgc cacttctttc accggcccaa   420
ccatacccgc atccactcgc aagcttatag accttatatc aggcttcgat actctgcgac   480
catgcttcgc accgggctcg gcagagacgt ggtgaaagcc gagccttagc ttgcttcgcg   540
tcctatgatg attccaccac cattgcctac acgacacgat acaccccgtac acgcccatgc   600 tacaccctgc ctacacacgc gcacacgcgc acaaacacac acatacatca acacacacaa   660
tacagcaatc cgtgcctctc tcttactcta ttcaagcgtg ctgcgtggcc tttgacttca   720
ttcctcttgt ccaccccgccg gccaccagta gaaccagcac cacgtccacc ctcatctcac   780
tcctctttcc cccacatccc ctactactcc atccttctca tctacagtca caccttcctc   840
ctcttcactt aacc                                                     854

<210> SEQ ID NO 7
<211> LENGTH: 1488
<212> TYPE: DNA
<213> ORGANISM: Nannochloropsis

<400> SEQUENCE: 7
aagcaagacg gaacaagatg gcacgcgtct gcaacagacc ggctcgcgcc gaacgtgcct    60
cctgcttttc aacgatcctg cgaggtcaac caggatttgc tcgccgggac gatttcatcc   120
ccttatcaac gagcccttga ggctccaggc gtgcttccac accccagttg gtaacaggac   180 attgggcat cttgcctatc ttgtcttagt gccgaaagcc tcaacgacct cccatggggt    240
ctgctcaacg cctcaacctt gcagtaagga tcccgaggg caagacccgc aaagccttct    300
gtcgtcggac aaagcggagc gagggaacag gctcagctca accctcttga gagcccataa   360
gtgccccctg atctatcttc aacagtcttt ccctgtcaca agaaaaccca gctagttgac   420
caagttgcta gagctgatac cttgtacttc gctctttgtg tgctttacct gattggacat   480
ggacagacct ccccttgctc ttccttctag gagcctggc tctcgctctt gttctttcga   540 gagcctttc ccttgagttg cgtatccagc gatcaagtat gaagagtgct ttcaaaccta   600
gatacgttct gcccagttct cttgcccttt tccacacgtg ctccacatct tcacacgact   660
```

| | |
|---|---:|
| cgcaccatac ccgacgaaac ccctcaaaac atcgcaacac ttacatcccg ctcgtgtccc | 720 |
| acccccgatg ccatatcctc tacagcagca gcaccaccac caccacttct taagtatggc | 780 |
| caagttgacc agtgccgttc cggtgctcac ccgcgcgcgac gtcgccggag cggtcgagtt | 840 |
| ctggaccgac cggctcgggt tctcccggga cttcgtggag gacgacttcg ccggtgtggt | 900 |
| ccgggacgac gtgaccctgt tcatcagcgc ggtccaggac caggtggtgc cggacaacac | 960 |
| cctggcctgg gtgtgggtgc gcggcctgga cgagctgtac gccgagtggt cggaggtcgt | 1020 |
| gtccacgaac ttccgggacg cctccggggcc ggccatgacc gagatcggcg agcagccgtg | 1080 |
| ggggcgggag ttcgccctgc gcgacccggc cggcaactgc gtgcacttcg tggccgagga | 1140 |
| gcaggactaa gcttctgtgg aagagccagt ggtagtagca gtagcagcag cagtagcagc | 1200 |
| cgcagcactc agtgttggcg cgagagattg tccatcccctt cttaacctac cggaagagaa | 1260 |
| ataaggcctt tctcccgtag ctgtcttcgt ttgtttgtgc tgattgcttg atatgagagt | 1320 |
| gttgaattcc tgcatcatgt ttttctctgt agtcctttcc taccccgtc attttctttt | 1380 |
| ctccctggtt cttcttttgt cacccttatt ttacataaaa ttttctttgt ttatagtgag | 1440 |
| aggaaggtag agagggaaa acaagaacaa cgaacgcaag cgtgtgaa | 1488 |

<210> SEQ ID NO 8
<211> LENGTH: 2318
<212> TYPE: DNA
<213> ORGANISM: Nannochloropsis

<400> SEQUENCE: 8

| | |
|---|---:|
| aagcaagacg gaacaagatg gcacgcgtct gcaacagacc ggctcgcgcc gaacgtgcct | 60 |
| cctgcttttc aacgatcctg cgaggtcaac caggatttgc tcgccgggac gatttcatcc | 120 |
| ccttatcaac gagcccttga ggctccaggc gtgcttccac accccagttg gtaacaggac | 180 |
| attgggcat cttgcctatc ttgtcttagt gccgaaagcc tcaacgacct cccatggggt | 240 |
| ctgctcaacg cctcaacctt gcagtaagga tccccgaggg caagacccgc aaagccttct | 300 |
| gtcgtcggac aaagcggagc gagggaacag gctcagctca accctcttga gagcccataa | 360 |
| gtgccccctg atctatcttc aacagtcttt ccctgtcaca agaaaaccca gctagttgac | 420 |
| caagttgcta gagctgatac cttgtacttc gctctttgtg tgctttacct gattggacat | 480 |
| ggacagacct cccccttgctc ttccttctag gagcctgggc tctcgctctt gttctttcga | 540 |
| gagacctttc ccttgagttg cgtatccagc gatcaagtat gaagagtgct ttcaaaccta | 600 |
| gatacgttct gccagttcct cttgcccttt tccacacgtg ctccacatct tcacacgact | 660 |
| cgcaccatac ccgacgaaac ccctcaaaac atcgcaacac ttacatcccg ctcgtgtccc | 720 |
| acccccgatg ccatatcctc tacagcagca gcaccaccac caccacttct taagtatggc | 780 |
| caagttgacc agtgccgttc cggtgctcac ccgcgcgcgac gtcgccggag cggtcgagtt | 840 |
| ctggaccgac cggctcgggt tctcccggga cttcgtggag gacgacttcg ccggtgtggt | 900 |
| ccgggacgac gtgaccctgt tcatcagcgc ggtccaggac caggtggtgc cggacaacac | 960 |
| cctggcctgg gtgtgggtgc gcggcctgga cgagctgtac gccgagtggt cggaggtcgt | 1020 |
| gtccacgaac ttccgggacg cctccggggcc ggccatgacc gagatcggcg agcagccgtg | 1080 |
| ggggcgggag ttcgccctgc gcgacccggc cggcaactgc gtgcacttcg tggccgagga | 1140 |
| gcaggactaa gcttctgtgg aagagccagt ggtagtagca gtagcagcag cagtagcagc | 1200 |
| cgcagcactc agtgttggcg cgagagattg tccatcccctt cttaacctac cggaagagaa | 1260 |
| ataaggcctt tctcccgtag ctgtcttcgt ttgtttgtgc tgattgcttg atatgagagt | 1320 |

-continued

| | |
|---|---|
| gttgaattcc tgcatcatgt ttttctctgt agtccttttcc taccccgtc attttctttt | 1380 |
| ctccctggtt cttcttttgt caccctttatt ttacataaaa ttttctttgt ttatagtgag | 1440 |
| aggaaggtag agaggggaaa acaagaacaa cgaacgcaag cgtgtgaatg ttctcaccat | 1500 |
| gtctcctgcc atggcccac gtcttgcgtc ggggctgtgg cgttttgaga atgggtgaca | 1560 |
| gggaagcgaa cacaggctaa gggagacgca tgcgtcggcg ggtctcgaca ctccacgcct | 1620 |
| tgtcggcaga aaggcgacgc acgagccaaa aagcactaga aggccttttc ttgggcatct | 1680 |
| tttctctgta cggccccta tcagcctgtc ttattgtgct ggtgttgctt gcgtgcgccc | 1740 |
| ttgacatcga ttactccggg aggctgcgcg gccgttgctt tggtcaacgt cgacacgaca | 1800 |
| cctctcccca acatgcacgg cagagtgatc ttcgggtgtg atgttgcgtg aacggccttt | 1860 |
| gtgccacttc tttcaccggc ccaaccatac ccgcatccac tcgcaagctt atagaccta | 1920 |
| tatcaggctt cgatactctg cgaccatgct tcgcaccggg ctcggcagag acgtggtgaa | 1980 |
| agccgagcct tagcttgctt cgcgtcctat gatgattcca ccaccattgc ctacacgaca | 2040 |
| cgatacaccc gtacacgccc atgctacacc ctgcctacac acgcgcacac gcgcacaaac | 2100 |
| acacacatac atcaacacac acaatacagc aatccgtgcc tctctcttac tctattcaag | 2160 |
| cgtgctgcgt ggcctttgac ttcattcctc ttgtccaccc gccggccacc agtagaacca | 2220 |
| gcaccacgtc caccctcatc tcactcctct ttccccacca tccctacta ctccatcctt | 2280 |
| ctcatctaca gtcacacctt cctcctcttc acttaacc | 2318 |

<210> SEQ ID NO 9
<211> LENGTH: 24
<212> TYPE: DNA
<213> ORGANISM: Nannochloropsis

<400> SEQUENCE: 9

| | |
|---|---|
| tgttctcacc atgtctcctg ccat | 24 |

<210> SEQ ID NO 10
<211> LENGTH: 54
<212> TYPE: DNA
<213> ORGANISM: Nannochloropsis

<400> SEQUENCE: 10

| | |
|---|---|
| acggcactgg tcaacttggc catggttaag tgaagaggag gaaggtgtga ctgt | 54 |

<210> SEQ ID NO 11
<211> LENGTH: 48
<212> TYPE: DNA
<213> ORGANISM: Nannochloropsis

<400> SEQUENCE: 11

| | |
|---|---|
| gaacaacgaa cgcaagcgtg tgaatgttct caccatgtct cctgccat | 48 |

<210> SEQ ID NO 12
<211> LENGTH: 31
<212> TYPE: DNA
<213> ORGANISM: Nannochloropsis

<400> SEQUENCE: 12

| | |
|---|---|
| ggttaagtga agaggaggaa ggtgtgactg t | 31 |

<210> SEQ ID NO 13
<211> LENGTH: 23
<212> TYPE: DNA
<213> ORGANISM: Nannochloropsis

```
<400> SEQUENCE: 13
atggccaagt tgaccagtgc cgt                                              23

<210> SEQ ID NO 14
<211> LENGTH: 24
<212> TYPE: DNA
<213> ORGANISM: Nannochloropsis

<400> SEQUENCE: 14
aagcaagacg gaacaagatg gcac                                             24

<210> SEQ ID NO 15
<211> LENGTH: 24
<212> TYPE: DNA
<213> ORGANISM: Nannochloropsis

<400> SEQUENCE: 15
ttcacacgct tgcgttcgtt gttc                                             24

<210> SEQ ID NO 16
<211> LENGTH: 775
<212> TYPE: DNA
<213> ORGANISM: Nannochloropsis

<400> SEQUENCE: 16
ggccccacgt cttgcgtcgg ggctgtggcg ttttgagaat gggtgacagg gaagcgaaca      60
caggctaagg gagacgcatg cgtcggcggg tctcgacact ccacgccttg tcggcagaaa     120
ggcgacgcac gagccaaaaa gcactagaag gccttttctt gggcatcttt tctctgtacg     180
gccccttatc agcctgtctt attgtgctgg tgttgcttgc gtgcgccctt gacatcgatt     240
actccgggag gctgcgcggc cgttgctttg gtcaacgtcg acacgacacc tctcccaac      300 atgcacggca gagtgatctt cgggtgtgat gttgcgtgaa cggcctttgt gccacttctt     360
tcaccggccc aaccataccc gcatccactc gcaagcttat agaccttata tcaggcttcg     420
atactctgcg accatgcttc gcaccgggct cggcagagac gtggtgaaag ccgagcctta     480
gcttgcttcg cgtcctatga tgattccacc accattgcct acacgacacg atacacccgt     540
acacgcccat gctacaccct gcctacacac gcgcacacgc gcacaaacac acacatacat     600
caacacacac aatacagcaa tccgtgcctc tctcttactc tattcaagcg tgctgcgtgg     660
cctttgactt cattcctctt gtccacccgc cggccaccag tagaaccagc accacgtcca     720
ccctcatctc actcctcttt cccccacatc cctactact ccatccttct catct           775
```